US012324568B2

(12) United States Patent
Xu et al.

(10) Patent No.: US 12,324,568 B2
(45) Date of Patent: Jun. 10, 2025

(54) MOUTHWASH TO DELIVER DYES FOR DENTAL IMAGING

(71) Applicants: Jian Xu, Baton Rouge, LA (US); Shaomian Yao, Baton Rouge, LA (US); Zhongqiang Li, Baton Rouge, LA (US)

(72) Inventors: Jian Xu, Baton Rouge, LA (US); Shaomian Yao, Baton Rouge, LA (US); Zhongqiang Li, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

(*) Notice: Subject to any disclaimer, the term of this patent is extended or adjusted under 35 U.S.C. 154(b) by 842 days.

(21) Appl. No.: 17/240,560

(22) Filed: Apr. 26, 2021

(65) Prior Publication Data
US 2021/0345870 A1    Nov. 11, 2021

Related U.S. Application Data

(60) Provisional application No. 63/016,202, filed on Apr. 27, 2020.

(51) Int. Cl.
*A61B 1/24* (2006.01)
*A61B 1/00* (2006.01)
*A61B 1/04* (2006.01)
*A61B 1/06* (2006.01)
*A61K 49/00* (2006.01)

(52) U.S. Cl.
CPC .............. *A61B 1/24* (2013.01); *A61B 1/0005* (2013.01); *A61B 1/043* (2013.01); *A61B 1/0638* (2013.01); *A61K 49/0034* (2013.01)

(58) Field of Classification Search
CPC ......... A61B 1/24; A61B 1/0005; A61B 1/043; A61B 1/0638; A61K 49/0034
See application file for complete search history.

(56) References Cited

U.S. PATENT DOCUMENTS 7,223,281 B2 * 5/2007 Altshuler ............... A61Q 11/00
                                                    607/90
8,647,119 B1 * 2/2014 Nagai .................. A61B 5/0088
                                                    433/29

(Continued)

OTHER PUBLICATIONS

ADA American Dental Association, "Mouthwash (Mouthrinse)", https://www.ada.org/en/member-center/oral-health-topics/mouthrinse#, updated Aug. 29, 2019 (1 page). (Accessed Jun. 17, 2021).

(Continued)

*Primary Examiner* — Baisakhi Roy
(74) *Attorney, Agent, or Firm* — Venable LLP; Keith G. Haddaway; Hemant Khanna

(57) ABSTRACT

A mouthwash for fluorescence endoscopic dental imaging includes at least one fluorescent dye and a liquid base. A method for fluorescent endoscopic dental imaging includes orally administering a mouthwash to a subject; waiting a predetermined period of time; removing excess mouthwash from the subject; illuminating the subject with visible or near-infrared light; and capturing fluorescent light from the subject to create an image.

16 Claims, 9 Drawing Sheets
(8 of 9 Drawing Sheet(s) Filed in Color)

(56) References Cited

U.S. PATENT DOCUMENTS

| | | | |
|---|---|---|---|
| 10,080,484 B2* | 9/2018 | Yang | G01N 21/6486 |
| 11,925,308 B2* | 3/2024 | Xu | A61B 1/0684 |
| 2008/0038686 A1* | 2/2008 | Nagai | A61B 5/0088 |
| | | | 433/29 |
| 2009/0075228 A1* | 3/2009 | Kumada | A61B 5/0088 |
| | | | 433/29 |
| 2009/0285766 A1* | 11/2009 | Kishen | A61K 6/52 |
| | | | 424/49 |
| 2009/0303317 A1* | 12/2009 | Tesar | H04N 5/33 |
| | | | 348/E7.085 |
| 2012/0172408 A1* | 7/2012 | Thyzel | A61K 6/69 |
| | | | 548/427 |
| 2014/0093457 A1* | 4/2014 | Nagai | A61K 6/65 |
| | | | 435/375 |
| 2014/0340287 A1* | 11/2014 | Achilefu | A61B 90/30 |
| | | | 345/8 |
| 2015/0216398 A1* | 8/2015 | Yang | A61B 1/00172 |
| | | | 600/109 |
| 2015/0216418 A1* | 8/2015 | Ammon | A61B 1/24 |
| | | | 433/29 |
| 2019/0046665 A1* | 2/2019 | Kossatz | A61K 49/0052 |
| 2019/0111168 A1* | 4/2019 | Bäumler | A61K 6/52 |
| 2019/0142700 A1* | 5/2019 | Baeten | A61C 13/20 |
| | | | 433/224 |
| 2019/0209590 A1* | 7/2019 | Ebetino | C07F 9/65583 |
| 2019/0328234 A1* | 10/2019 | Seibel | A61B 5/14539 |
| 2020/0390909 A1* | 12/2020 | Harmsen | A61K 49/0032 |
| 2022/0008157 A1* | 1/2022 | Maier-Hein | A61B 5/1455 |
| 2022/0167853 A1* | 6/2022 | Nikinmaa | A61B 5/0071 |

OTHER PUBLICATIONS

American Dental Association and US Food and Drug Administration "Dental radiographic examinations: recommendations for patient selection and limiting radiation exposure", (2012) (29 pages).

Bagchi et al., "Evaluation of efficacy of a commercially available herbal mouthwash on dental plaque and gingivitis: A double-blinded parallel randomized controlled trial", Journal of Indian Association of Public Health Dentistry, (2015), vol. 13, pp. 222-227.

Banerji et al., "Cracked tooth syndrome. Part 1: aetiology and diagnosis", Br Dent J., (2010), vol. 208, No. 10, pp. 459-463.

Bolouri et al., "Performance of orthopantomography, planar scintigraphy, CT alone and SPECT/CT in patients with suspected osteomyelitis of the jaw", Eur J Nucl Med Mol Imaging., (2013), vol. 40, pp. 411-417.

Buhler et al., "Imaging of occlusal dental caries (decay) with near-IR light at 1310-nm", Opt Express., (2005), vol. 13, pp. 573-582.

Chung et al., "Multispectral near-IR reflectance and transillumination imaging of teeth", Biomed Opt Express., (2011), vol. 2, pp. 2804-2814.

Chung et al., "Near infrared imaging of teeth at wavelengths between 1200 and 1600 nm", Proc SPIE Int Soc Opt Eng., (2011), 7884 (11 pages).

Dubey et al., "Evaluation of novel mouthwash on dental remineralization", Evaluation, (2018), vol. 4, pp. 167-169.

Erten et al., "Restorative treatment decision making with unaided visual examination, intraoral camera and operating microscope", Operative dentistry, (2006), vol. 31, pp. 55-59.

Fried et al., "Near-IR imaging of cracks in teeth", Proc SPIE Int Soc Opt Eng., (2014), 8929: 89290Q, (11 pages).

Guerrero et al., "The diagnostic efficacy of cone beam CT for impacted teeth and associated features: a systematic review", J Oral Rehabil. (2011), vol. 38, pp. 208-216.

Hasan et al., "Cracked tooth syndrome: Overview of literature", Int J Appl Basic Med Res., (2015) vol. 5, Iss. 3, pp. 164-168.

Jones et al., "Near-infrared transillumination at 1310-nm for the imaging of early dental decay", Opt Express., (2003), vol. 11, pp. 2259-2265.

Kahler et al., "The cracked tooth conundrum: terminology, classification, diagnosis, and management", Am J Dent., (2008), vol. 21, pp. 275-282.

Kawase et al., "Cerebral abscess following the self-extraction of teeth in patient with Ebstein's anomaly: a case report", BMC Oral Health. (2019) vol. 19: 200 (5 pages).

Kiljunen et al., "Dental cone beam CT: A review", Phys Med., (2015), vol. 31, pp. 844-860.

Lee et al. "Nondestructive assessment of the severity of occlusal caries lesions with near-infrared imaging at 1310 nm", J Biomed Opt., (2010), vol. 15, No. 4, pp. 047011-1-047011-7.

Lee et al., "Dental optical coherence tomography: new potential diagnostic system for cracked-tooth syndrome", Surg Radiol Anat., (2016), vol. 38, pp. 49-54.

Li et al., "Endoscopic near-infrared dental imaging with indocyanine green: a pilot study", Ann N Y Acad Sci., (2018), vol. 1421, pp. 88-96.

Li et al., "Indocyanine green-assisted dental imaging in the first and second near-infrared windows as compared with X-ray imaging", Ann N Y Acad Sci., (2019), vol. 1448, pp. 42-51.

Li et al., "Indocyanine-green-assisted near-infrared dental imaging-the feasibility of in vivo imaging and the optimization of imaging conditions", Scientific reports., (2019), vol. 9, 8238 (9 pages).

Li et al., Cover Image, Ann N Y Acad Sci.(2019),vol. 1448, Issue 1. 1448: i-i.

Mathew et al., "Diagnosis of cracked tooth syndrome", J Pharm Bioallied Sci., (Aug. 2012), vol. 4, Suppl. 2, pp. S242-S244.

Pereira et al., "Taking advantage of an unerupted third molar: a case report", Dental Press J Orthod., (2017), vol. 22, pp. 97-101.

Sener et al., "Non-Syndromic Familial Unerupted Teeth: A Rare Contidion", Cumhuriyet Dental Journal, (2013), vol. 18, Iss. 4, pp. 359-363.

Seo et al., "Analysis of factors associated with cracked teeth", J Endod., Mar. 2012, vol. 38, pp. 288-292.

Shah et al., "Recent advances in imaging technologies in dentistry", World J Radiol., (Oct. 28, 2014), vol. 6, No. 10, pp. 794-807.

Sheiham, "Oral health, general health and quality of life", Bulletin of the World Health Organization, Sep. 2005, vol. 83, No. 9, pp. 644-645.

Simon et al., "Near-infrared imaging of secondary caries lesions around composite restorations at wavelengths from 1300-1700-nm", Dent Mater., (2016), vol. 32, pp. 587-595.

Simon et al., "Transillumination and reflectance probes for in vivo near-IR imaging of dental caries", Proc SPIE Int Soc Opt Eng., (2014), 8929: 89290D (16 pages).

Staninec et al., "In vivo near-IR imaging of approximal dental decay at 1,310 nm", Lasers Surg Med., (2010), vol. 42, pp. 292-298.

Staninec et al., "Non-destructive clinical assessment of occlusal caries lesions using near-IR imaging methods", Lasers Surg Med., (2011), vol. 43, pp. 951-959.

Tymofiyeva et al., "Three-dimensional localization of impacted teeth using magnetic resonance imaging", Clin Oral Investig., (2010) vol. 14, pp. 169-176.

Usenik et al., "Automated Classification and Visualization of Healthy and Diseased Hard Dental Tissues by Near-Infrared Hyperspectral Imaging", Applied Spectroscopy., (2012), vol. 66, pp. 1067-1074.

Vandenberghe et al., "Modern dental imaging: a review of the current technology and clinical applications in dental practice", Eur Radiol. (2010), vol. 20, pp. 2637-2655.

Wu et al., "High contrast near-infrared polarized reflectance images of demineralization on tooth buccal and occlusal surfaces at lambda ? = 1310-nm", Lasers Surg Med., (2009), vol. 41, pp. 208-213.

Yadav et al., "Dental caries: A review", Asian Journal of Biomedical and Pharmaceutical Sciences, Jan. 2016, vol. 6, pp. 01-07.

* cited by examiner

MOUTHWASH TO DELIVER DYES FOR DENTAL IMAGING

PRIORITY

This application claims priority to provisional application 63/016,202 filed Apr. 27, 2020.

BACKGROUND

1. Technical Field

Embodiments of the invention relate generally to dental imaging, and more particularly, to a mouthwash to deliver dyes for dental imaging.

2. Discussion of Related Art

The field of oral health has attracted significant interest due to a large amount of the human population suffering from various dental diseases and disorders, such as caries lesions, cracked teeth, impacted teeth, etc.[1] Over 60-90% of school-aged children and most adults are influenced by various types of caries lesions, which are considered a primary cause of oral pain and tooth loss.[2] Impacted teeth (partial or complete failure of eruption), especially for the third molar (commonly known as the wisdom tooth), affects 25% to 50% of the population.[3-5] Tooth cracks cause the loss of sound tooth structures[6-8] and have a high incidence, affecting 34%-74% of adults.[9] A cracked tooth, however, is notoriously difficult to diagnose even for experienced dentists.[10] Common to the above dental diseases is that they are chronic; therefore, early detection is necessary for preventing their development into more advanced dental diseases. Untreated tooth cracks and caries are the most common causes leading to severe tooth infections, including tooth abscess, and even tooth extractions.[11]

Dental imaging plays an important role in the screening and diagnosis of dental diseases. There are several conventional imaging modalities commonly used in dentistry, including visual inspection, dental X-ray imaging (e.g. 2D radiograph), magnetic resonance imaging (MRI), and ultrasound. Other than visual inspection, X-ray imaging is most commonly used in the clinic.[12-15] Cone-beam computed tomography (CBCT) can reconstruct the 3D dental structures of the tooth, which could significantly improve the accuracy of evaluating dental diseases for pre-surgical assessment.[4, 16] However, the ionizing radiation produced by X-ray carries a potential risk to the patient,[13-15] and CBCT has a 3 to 44 times higher radiation dosage than panoramic radiograph (2D images).[16] Other imaging approaches, like MRI, are limited by their costliness or their ability to easily miss internal dental diseases.[15, 17, 18] Accordingly, improved imaging modalities are needed for dental screening and diagnosis.

SUMMARY

According to embodiments of the invention, a mouthwash for fluorescent endoscopic dental imaging is disclosed, which contains at least one fluorescent dye and a liquid base. In an embodiment of the invention, the least one fluorescent dye fluoresces under near-infrared light.

In an embodiment of the invention, the mouthwash liquid base contains water, medical normal saline solution made from sodium chloride, or any commercial mouthwash antiseptic solution. Other commercial mouthwash solutions may include, for example, ethanol, menthol, sorbitol, glycerin, and/or xylitol, as well as other components.

In some embodiments, the at least one fluorescent dye is indocyanine green (ICG). In embodiments of the invention, the concentration of the at least one fluorescent dye in the mouthwash is a 50 µM-1.3 mM ICG.

According to embodiments of the invention, a method for fluorescent endoscopic dental imaging is disclosed. To carry out the method, mouthwash is orally administered to a subject, followed by waiting a predetermined period of time; the mouthwash is then removed from the subject; the subject is then illuminated with visible or near-infrared light; and fluorescent light from the subject is captured to create an image. In some embodiments of the invention, the predetermined period of mouthwash time is about 1 minute. In embodiments of the invention, the captured fluorescent light from the subject creates an image which captures a two-dimensional near-infrared dental image of the subject.

In some embodiments of the invention, the subjected is instructed to not ingest the mouthwash. In some embodiments of the invention, the amount of mouthwash administered to the human subject is about 8-400 mL, about 8-100 mL, about 8-50 mL, about 50-200 mL, about 100-200 mL, about 50 mL, about 100 mL or about 150 mL. In embodiments of the invention, the amount of mouthwash administered should be sufficient to deliver an effective dosage of dye of 0.1-5 mg/kg (body weight) ICG. For example, a suitable concetration to achieve the dosage is 100 nM-1.3 mM. In embodiments of the invention, the subject is illuminated with near-infrared light.

In some embodiments of the invention, the method does not include subcutaneous or intravenous administration of a contrast agent. In some embodiments, the method does not include the use of ionizing-radiation materials.

In embodiments of the invention, the method for fluorescent endoscopic dental imagining also includes analyzing the fluorescent light to create a spectroscopic signal, and displaying a two-dimensional fluorescent dental image. In some embodiments, the method also includes displaying spectroscopic data corresponding to the spectroscopic signal.

In some embodiments of the invention, the method includes analyzing the fluorescent light to identify cracks or caries lesions in a tooth of the subject.

In some embodiments of the invention, the imaging is done in a first near-infrared (NIR) window (700-950 nm), a second NIR window (1000-1700 nm), or a combination thereof.

Further objectives and advantages will become apparent from a consideration of the description, drawings, and examples.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements.

DETAILED DESCRIPTION

Figure 1:
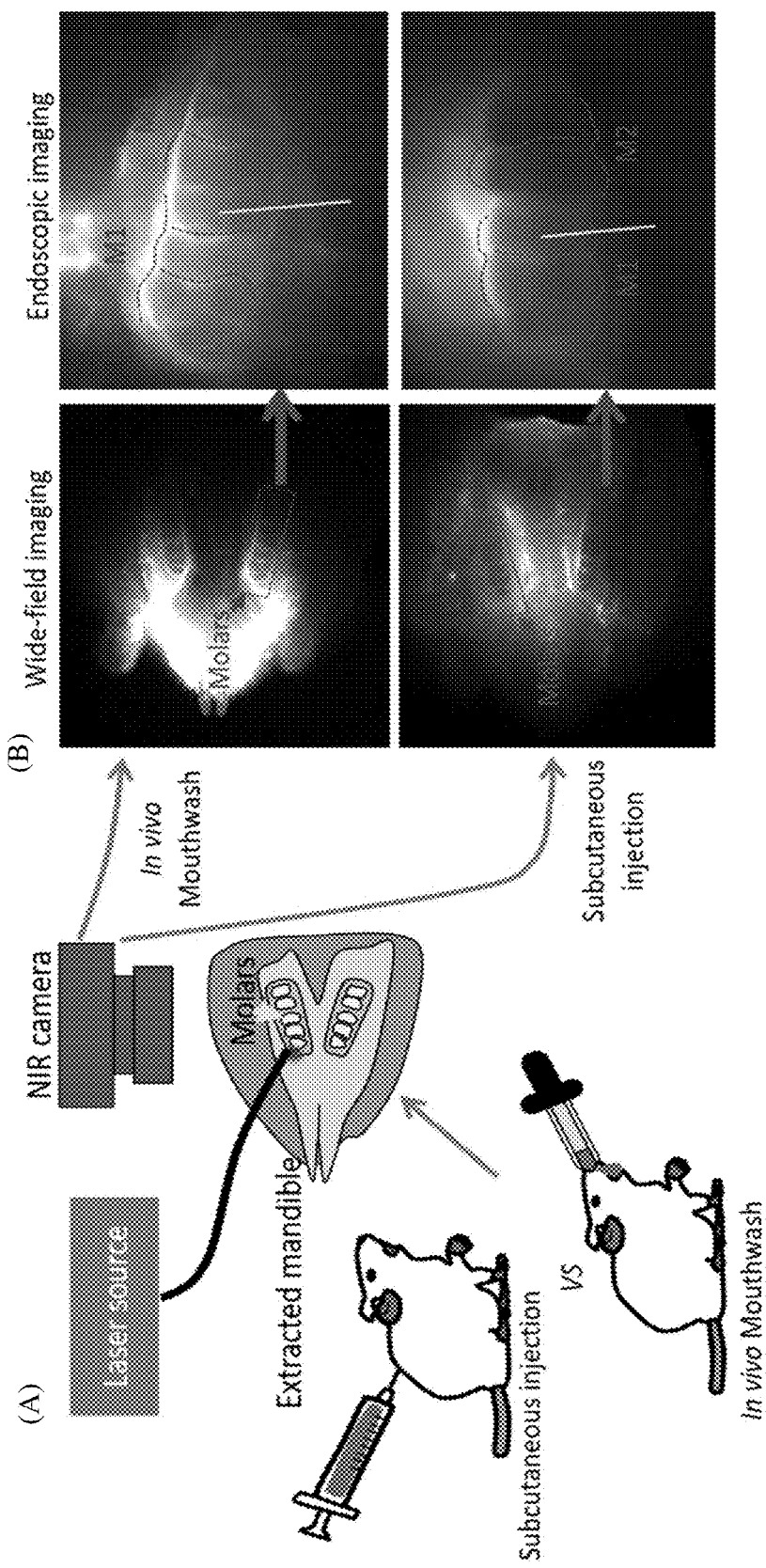
FIG. 1 shows a schematic diagram of the indocyanine green (ICG)-assisted NIR dental imaging with the rat model, and ICG-assisted NIR I images. (A) shows a schematic diagram of experimental procedures; (B) depicts ICG-assisted NIR I images of rat mandibles with in vivo mouthwash vs. subcutaneous injection under wide-field imaging and endoscopic imaging. M1: first molar; M2: second molar.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Near-infrared (NIR) transillumination has gradually become attractive, owing to its high contrast, high sensitivity, affordable cost, and easy-to-use approach.[19-25] While wavelengths in the NIR field range from 1000 nm to 2000 nm,[22, 24, 25] the wavelength of 1310 nm is considered to be an optimal NIR wavelength for diagnosing caries because it yields the highest image contrast between the enamel and dentin.[20, 26-28] Previous work[29-31] extended the NIR dental imaging to the first near-infrared (NIR) window (700-950 nm) with the help of the FDA-approved fluorescence dye, indocyanine green (ICG). It has also been demonstrated that ICG can be used for dental imaging in the second NIR window (1000-1700 nm).[32] However, one limitation was that the ICG agent was administered by subcutaneous or intravenous injection, which limits the applicability of our method for human patients.

Mouthwash, also called mouth rinse, is routinely used to maintain oral hygiene to reduce the risk of cavities and gum disease.[33] Currently, commercial mouthwash is used in the therapy of dental diseases, like dental remineralization[34] or dental plaque and gingivitis.[35] Nevertheless, few studies have demonstrated the feasibility of the mouthwash method for NIR dental imaging, particularly with the ICG agent, that can image below the surface of tissue.

In previous work with human extracted teeth,[32] the teeth were immeresed in an ICG solution for time intervals of 10 minutes and 24 hours. Clear ex vivo dental structures were obtained. This previous method can detect even tiny cracks that were not visible in dental X-ray. This result supported the hypothesis that mouthwash could be an effective way to deliver the ICG for ICG-assisted dental imaging. The present disclosure validates the feasibility of ICG-assisted in vivo dental imaging with mouthwash using rats as an animal model, and further optimized dental imaging using extracted human teeth. The term "fluorescent dental imaging" may refer to imaging using visible light and/or imaging using near-infrared light.

According to some embodiments of the invention, a mouthwash for fluorescent endoscopic dental imaging includes at least one fluorescent dye and a liquid base. The liquid base may include, for example, solutions such as water, medical normal saline solution made from sodium chloride, or any commercial mouthwash antiseptic solution. Other Commercial mouthwash antiseptic solutions may include as ethanol, menthol, sorbitol, glycerin, xylitol, and other ingredients.

Examples of the at least one fluorescent dye, include ICG, fluorescein, methylene blue, or 5-ALA. According to some embodiments, the at least one near-infrared fluorescent dye is ICG. The concentration of at least one near-infrared fluorescent dye in the mouthwash may be 0.1-5 mg/kg (body weight) ICG for in vivo mouthwash or 100 nM-1.3 mM; for example, 1.0 μM-1.3 mM, 10 μM-1.3 mM, 50 μM-1.3 mM, 1.0 μM-100 μM, 1.0 μM-10 μM, or 10 μM-100 μM ICG solution for ex vivo mouthwash, or 100 μM-about 1.3 mM ICG solution Other FDA approved fluorescent dyes, such as fluorescein (<14 mg/kg), methylene blue (5 mg/kg), and 5-ALA (5-Aminolevulinic acid, (300 mg/kg), can also be delivered by this mouthwash method for dental imaging. The subject may hold the dye-containing mouthwash in their mouth for a while (e.g. 1-15 sec), either gargling or not, then spit to prepare for imaging. The mouthwash solutions may be safe even to be accidentally swallowed.

According to some embodiments of the invention, a method for fluorescent endoscopic dental imaging includes orally administering a mouthwash to a subject. The method includes waiting a predetermined period of time, and removing excess mouthwash from the subject. The method includes illuminating the subject with visible or near-infrared light, and capturing fluorescent light from the subject to create an image.

The predetermined period of time according to some embodiments is about 1 minute. In some embodiments, the predetermined period of time is at least about 1 minute. In some embodiments, the predetermined period of time is about 15 seconds to about 90 seconds, about 15 seconds to about 60 seconds, or about 15 seconds to about 30 seconds. Administering the mouthwash may further include instructing the subject not to ingest the mouthwash. The method does not require administering a contrast agent subcutaneously or intravenously and, preferably, does not include administering a contrast agent subcutaneously or intravenously. According to some embodiments, the amount of mouthwash is about 8-400 ml for a human subject or 10-100 μl for a rat or a mouse, to reach the effective dosage of dye, such as 0.1-5 mg/kg (body weight) ICG. In some embodiments of the invention, the amount of mouthwash administered to the human subject is about 8-400 mL, about 8-100 mL, about 8-50 mL, about 50-200 mL, about 100-200 mL, about 50 mL, about 100 mL or about 150 mL. A high concentration of ICG may be used, such as 1.3 mM, to reduce the volume of mouthwash solution to be taken. Solutions of lower concentration may also be used, but with increased volume of mouthwash solution. An appropriate amount may be given to reach the effective final dosage (0.1-5 mg/kg). According to some embodiments, capturing fluorescent light from the subject to create an image comprises capturing a two-dimensional near-infrared dental image of the subject. According to some embodiments, the method for fluorescent endoscopic dental imaging includes analyzing the fluorescent light to create a spectroscopic signal, and displaying a two-dimensional near-infrared dental image. According to some embodiments, the method further includes displaying spectroscopic data corresponding to the spectroscopic signal.

The method does not use ionizing-radiation materials. According to some embodiments, the method for fluorescent endoscopic dental imaging further includes analyzing the near-infrared light to identify cracks or caries lesions in a tooth of the subject.

In previous work,[29-32, 36] the feasibility of ICG-assisted NIR dental imaging was demonstrated in a rat model and human extracted teeth. For the rat model, the profiles of the erupted and unerupted molars (only postnatal day 9) were observed clearly at short imaging window (10 minutes). In particular, the unerupted molar had a much larger imaging window (about 96 hours) than that of the erupted molars (4 hours). For the human extracted teeth, the common dental disorders and diseases, (e.g. caries lesion, crack, and decay) were observed clearly from NIR dental fluorescence images; cracks, which are often missed by common dental X-ray and CT, were clearly visible. Additionally, exploration of human dental images with the first and second imaging window showed that both imaging windows reflect good image contrast.

Figure 2:
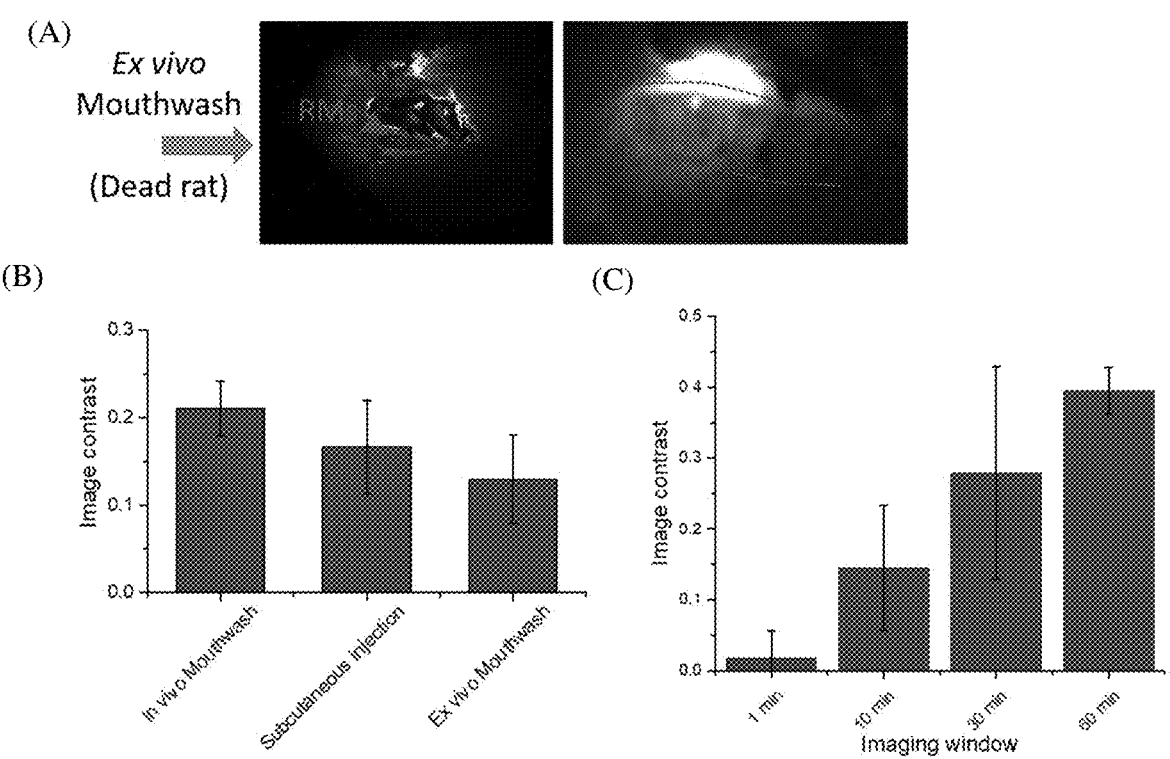
FIG. 2 shows image contrast of ICG-assisted dental imaging with the euthanized rat. (A) shows ex vivo mouthwash with the euthanized rat. RMs: right molars; (B) shows the image contrast of ICG-assisted dental imaging with in vivo mouthwash, subcutaneous injection, and ex vivo mouthwash; (C) shows the image contrast of rat teeth by ex vivo mouthwash at different imaging windows.

The extracted first molar of a rat was clearly identified when immersed 30 minutes in ICG solution and the image contrast was 0.65; while the image contrast of human tooth was around 0.8 after only 1 min-immersion. The human teeth seemed to absorb ICG more easily than rat molar. In addition, in vivo mouthwash took less time (1-2 minutes) than the dead ex vivo mouthwash (near 30 minutes) to achieve the same image contrast in the rat model (FIGS. 1 and 2). Consequently, it was rational to infer that human teeth can be imaged in vivo through the mouthwash method with short time (<1 min).

Figure 9:
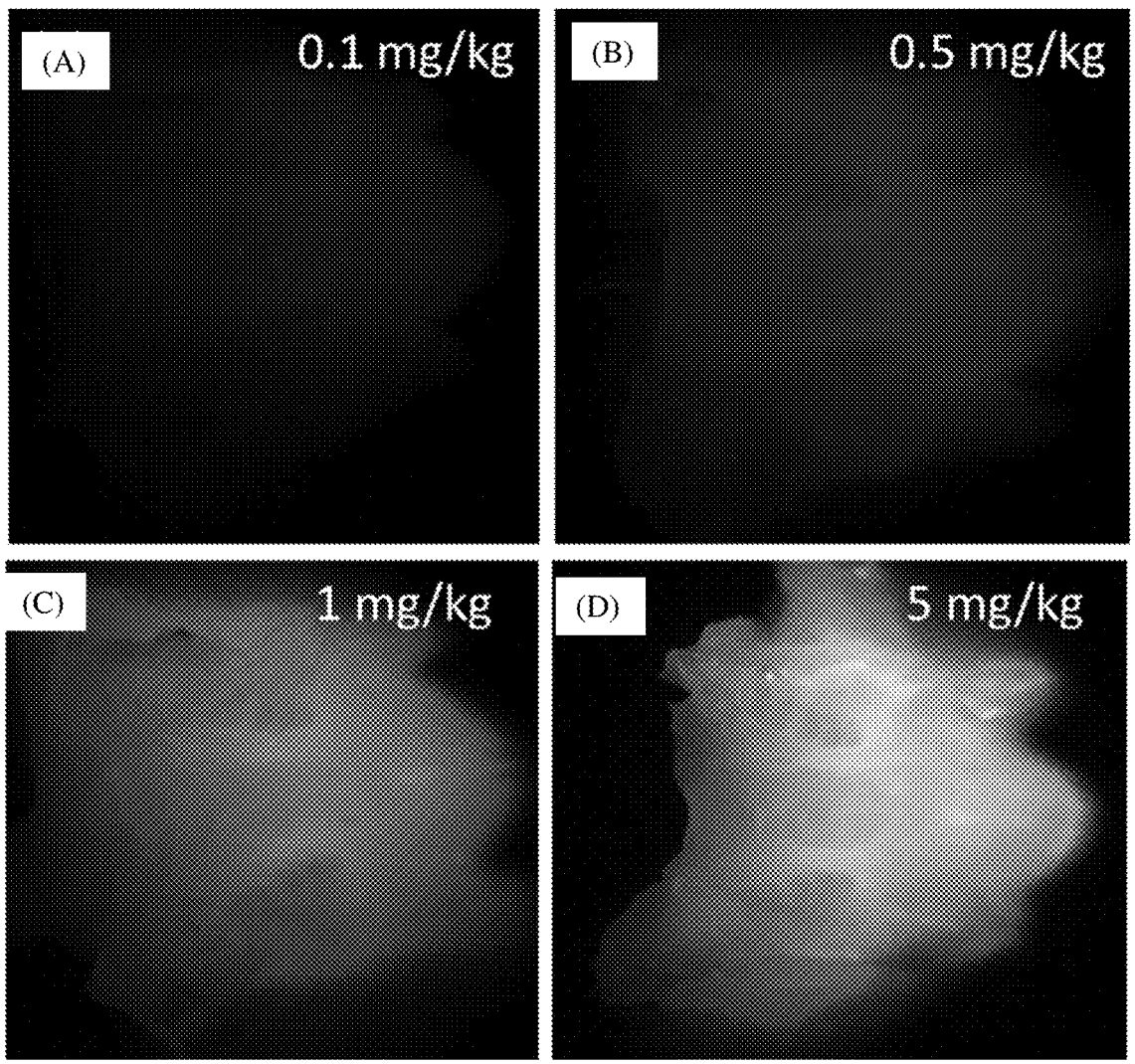
FIG. 9 shows ICG-assisted dental imaging with different ICG injection dosages. (A) shows ICG-assisted dental imaging with an ICG injection dosage of 0.1 mg/kg; (B) shows ICG-assisted dental imaging with an ICG injection dosage of 0.5 mg/kg; (C) shows ICG-assisted dental imaging with an ICG injection dosage of 1 mg/kg; (D) shows ICG-assisted dental imaging with an ICG injection dosage of 5 mg/kg.

The mouthwash delivery of dye has a good efficiency for the erupted molars; the molars could be seen from the wide-field imaging and the endoscopic imaging. However, mouthwash requires a much lower dosage of dye to achieve similar image contrast, for example when imaging unerupted molars that are covered by surface tissues and cannot be clearly observed by traditional visible inspection. The minimal dye dosage of subcutaneous injection is 0.1 mg/kg (body weight) to achieve recognizable anatomical imaging (FIG. 9); in the mouthwash, the dosage was only 10 L ICG solution (1 mg/ml), around 0.01 mg/kg for the P14 rat, which is 50 times lower than the amount required for subcutaneous injection (0.5 mg/kg) (FIG. 9) and at this concentration the molars were clearly observed (FIG. 2(B)). The molars became more distinguishable when the injection concentration increased above 1 mg/kg which was 100 times larger than mouthwash. Thus, mouthwash could provide a more friendly, convenient, and pain-free method for dye delivery in dental imaging.

In previous rat research, subcutaneous injection was employed to deliver the ICG, which may cause extra pain. In human dentistry, the visual inspection of the tooth is useful, especially when using gentian violet or methylene blue stains to highlight fracture lines.[37, 38] This procedure, however, requires the placement of a provisional restoration to the patient cavity and takes about 2-5 days to be effective.[37] According to the present invention, mouthwash is an appropriate vehicle to deliver ICG in vivo in living rats. The results disclosed herein show that the mouthwash achieves better imaging quality and image contrast, with shorter imaging window than subcutaneous injection. The present invention provides for a mouthwash as a valuable approach for the delivery of dye when using ICG-assisted NIR dental fluorescence imaging in human dentistry. ICG-assisted NIR dental imaging as disclosed herein represents a painless and real-time imaging tool without the risk of ionizing radiation.

The present invention shows that both the erupted and unerupted molars have a good image contrast at short imaging window. For erupted molars (P31 rats), no dental structures were observed 24 hours after ICG injection, but the unerupted molars still had a high image contrast even 48 hours after ICG injection, and the molar regions became brighter than the surrounding tissues. Although the real dental structures could also be reconstructed accurately using 3D X-ray imaging,[13-15] microCT has a much higher ionizing radiation dosage than 2D radiography. Nonetheless, the present invention's approach to endoscopic dental imaging provides similar morphologies of dental structures as depicted in 3D X-ray images, but without ionizing-radiation related health risks.

Diagnosis of some dental diseases, like cracked teeth and small caries lesions, is extremely challenging due to their asymptomatic presentation and inefficient diagnostic tools. Early diagnosis is beneficial in preventing further progress of these diseases. Compared to visible light, NIR light (700-2000 nm) has a much lower scattering coefficient in normal enamel, and NIR photons penetrate much deeper, through the tooth enamel. Therefore, many existing studies operate NIR dental imaging in the second NR window in order to image caries lesions and cracks with a higher contrast. In particular, 1310 nm yields the highest image contrast between enamel and dentin, which will help in diagnosing cracks and caries lesions.

With the help of ICG agents, dental imaging according to the present invention is effective in both the first and second NIR windows. The enamel and dentin are distinguishable in both NIR windows. It is more challenging to identify the enamel and dentin with short ICG immersion, since the image contrast increases with imaging windows. Specifically, the enamel and dentin were not distinguishable after 1 minutes of ICG immersion, but were easily recognizable after 24 hours of ICG immersion. This result indicates ICG molecules can gradually and differently penetrate the tooth enamel and dentin; a lower scattering coefficient of NIR photons in the sound enamel yields the image contrast between the enamel and dentin.

Identifying cracks in teeth is extremely challenging with current imaging modalities. For example, even with a resolution of 16 μm, microCT failed to detect enamel cracks (FIG. 7); in contrast, the cracks were distinguished clearly with the present invention's approach in the first and second NIR window. Further, caries lesion became a bright dot under the first NIR window, however, the lesion was more difficult to observe under the second NIR window. This is mainly because the NIR II camera has a much lower pixel resolution than the NIR I camera, and the InGaAs sensor (NIR II camera) is comparatively more expensive (almost 10 times) than CCD and CMOS cameras (NIR II camera).[39] Even so, the imaging system according to the present invention shows that the NIR I camera could achieve much better imaging quality than the NIR II camera. Thus, ICG-assisted mouthwash dental imaging represents a low-cost dental imaging method for the diagnosis of dental diseases and disorders (e.g., cracks and caries).

The present invention discloses the feasibility of ICG-assisted dental imaging using mouthwash in living rats. In a rat model mouthwash delivery of ICG produces a better image contrast than subcutaneous injection for erupted molars at short imaging window (less than 1 minute). Endoscopic dental imaging with mouthwash obtained a similar profile of the molar as the 3D X-ray imaging; the method of the present invention also depicts the molars for the unerupted molars that cannot be seen through wide-field imaging. For human teeth, clear profiles are obtained in as short as 1 minute of ICG immersion. The image contrast between the enamel and dentin yielded the largest image contrast after 24 hours of ICG immersion in the first and second NIR windows. A caries lesion became a bright dot and easier to identify in the first NTR windows. Use of in vivo mouthwash delivery for human dental imaging shows teeth distinctly and caries as a bright dot; and mouthwash with endoscopic imaging can image the unerupted wisdom teeth more efficient with lower dosage and shorter imaging time. Overall, the mouthwash is an unexpected alternative method for ICG delivery, and ICG-assisted NIR dental fluorescence imaging provides a low-cost, safe, real-time dental imaging tool for the diagnosis of dental diseases without ionizing radiation risks.

EXAMPLES

Animals

Self-breed Sprague Dawley rats, including eight postnatal day 31 (P31) and two P21 rats for erupted molars and sixteen P14 rats for unerupted molars, were utilized. To simulate the mouthwash with living rats, 10 μL ICG solution (1 mg/ml) was pipetted into the mouth of two P31 rats in vivo, and the rats were euthanized after 2 minutes. The other two P21 went through the same in vivo mouthwash procedure and euthanized after 1 minute. In addition, the mandibles were dissected from another two P31 rats directly after euthanasia, then washed with 10 μL ICG (1 mg/ml) solution ex vivo for 10 minutes. For the subcutaneous injection, every two P31 rats were euthanized at each time points 10 minutes and 24 hours, for the ICG injection on the back (5 mg/kg body weight). For the unerupted molars, two rats were sacrificed 1 minute after in vivo mouthwash, and the same for the erupted molars. To study concentration effect on imaging, 0.1, 0.5, 1, and 5 mg/kg of ICG were injected into eight P14 rats (two rats for each dosage, and euthanized for each concentration 4 hours after injection). For P14 rats to study imaging windows, two rats were euthanized at 10 minutes, 4 hours and 48 hours for posting ICG injection (5 mg/kg) respectively. Table 1 shows the rat distributions.

TABLE 1

Experimental conditions of rat dental models

| Num | Rat | Method | Imaging windows | ICG dosage |
| --- | --- | --- | --- | --- |
| 2 | P31 | in vivo MW | 2 mins | 10 μL (1 mg/ml) |
| 2 | P31 | ex vivo MW | 2 mins | 10 μL (1 mg/ml) |
| 4 | P31 | SI | 10 mins (2), 24 hrs (2) | 5 mg/kg body weight |
| 2 | P21 | in vivo MW | 1 min | 10 μL (1 mg/ml) |
| 2 | P14 | in vivo MW | 1 min | 10 μL (1 mg/ml) |
| 8 | P14 | SI | 4 hrs | 0.1, 0.5, 1, 5 mg/kg (2 of each) |
| 6 | P14 | SI | 10 mins (2), 4 hrs (2), 24 hrs (2) | 5 mg/kg body weight |

Note:
1) P31 and P21 were erupted molars, P14 were unerupted molars.
2) MW: mouthwash, SI: subcutaneous injection The imaging system is depicted in FIG. 1(A). A 785 nm laser source shined to the mandibles with fiber and filters, a NIR camera received the videos, and videos were recorded by computer. The mandibles were then extracted and imaged using ICG-assisted endoscopic NIR dental imaging, as described in previous publications.[29-31] In the endoscopic imaging, an output fiber was connected to the endoscope with a camera.[30] All experiments were approved by the Institutional Animal Care and Use Committee (IACUC) of Louisiana State University (Protocol #16-117) and followed the ethical guidelines of animal care.

Human Teeth

Thirty-two human teeth were collected from the Louisiana State University Health Science Center (LSUHSC)—Department of Oral & Maxillofacial Surgery (Baton Rouge, USA), and the diseases were confirmed by Dr. Waleed Zaid. All the samples were fixed in a 10% neutral buffer formalin solution overnight and then washed with phosphate buffered saline (PBS) solution. Prior to the dental imaging, the teeth were immersed into 50 μM ICG solution. To compare the ex vivo mouthwash effects on human and rat teeth, extracted rat teeth from ICG-free rats were also immersed into 50 μM ICG solution. To optimize the imaging window (the time difference between ICG injection and observation), four teeth were removed from the solution and imaged at designated time points of 1 minute, 10 minutes, 30 minutes, 1 hour, 4 hours, 6 hours, 15 hours, and 24 hours using the method of the invention.

The imaging platform for the human teeth was previously described.[32] The experiments were approved by the Institutional Review Board of Louisiana State University (IRB #E11061).

X-Ray Dental Imaging

After the ICG dental imaging, the human teeth and rat mandibles were scanned with a three-dimensional (3D) microCT (SCANCO Medical AG, model μCT 40) under the conditions of 55 kV, 144 μA, 300 ms with the thickness of the CT slices set to 16 μm. The 3D reconstruction of the extracted mandibles and human teeth was performed in the Avizo Software Version 9.4.0 (Thermo Fisher Scientific).

Results

Comparison of Mouthwash and Subcutaneous Injection to Deliver ICG for Dental Imaging in Rat Model This work used the P31 rats with erupted molars to compare the efficacy of using mouthwash and subcutaneous injection to deliver the ICG for ICG-assisted dental imaging (FIG. 1). Rat dental structures were imaged at 2 minutes after in vivo mouthwash or 10 minutes after subcutaneous injection. The profiles of three occlusal cusps of the first molars (M1) and two cusps of the second molars (M2) were clearly recognized using wide-field imaging in NIR fluorescence mode (FIG. 1(B)).

Meanwhile, endoscopic imaging provided clearer morphologies of the first and second molars than wide-field imaging. The lingual and occlusal cusps of the molars could be easily distinguished, especially for the mouthwash treatment (FIG. 1(B)). As described in previous work,[29, 30] the intensity-mean difference $D_{mean\_diff}$ (IMD) was used as the image contrast for the quantitative evaluation of the target and background. To further reveal the efficiency of the mouthwash and local injection, a sampling line (yellow lines in FIG. 1) covering both molar regions and the surrounding tissues was used to calculate the image contrast of the molar and surrounding tissues. If the ICG mouthwash was applied ex vivo to the extracted rat mandibles, dental structures were imaged with less favorable contrast than that from in vivo mouthwash in the same imaging window (FIG. 2(A), (B)); however, the image contrast from ex vivo mouthwash can be improved, to be comparable to that of in vivo mouthwash with shorter imaging window, by prolonging the waiting time before imaging (FIG. 2(C)).

Meanwhile, to further explore the influence of the mouthwash on the imaging quality of the unerupted and erupted molars and shorten the imaging time, one P14 rat (unerupted molar) and one P21 rat (erupted molar) were administered 10 μl ICG through mouthwash; after 1 min the two rats were euthanized and imaged under ICG-assisted dental imaging with wide-field imaging and endoscopic imaging. In the endoscopic imaging, the profiles of the first molar became recognizable and its three cusps could be distinguished for the unerupted molar (FIG. 3(C)); the erupted molar was more clearly recognized from ICG-assisted NIR images (FIG. 3(D)).

Figure 3:
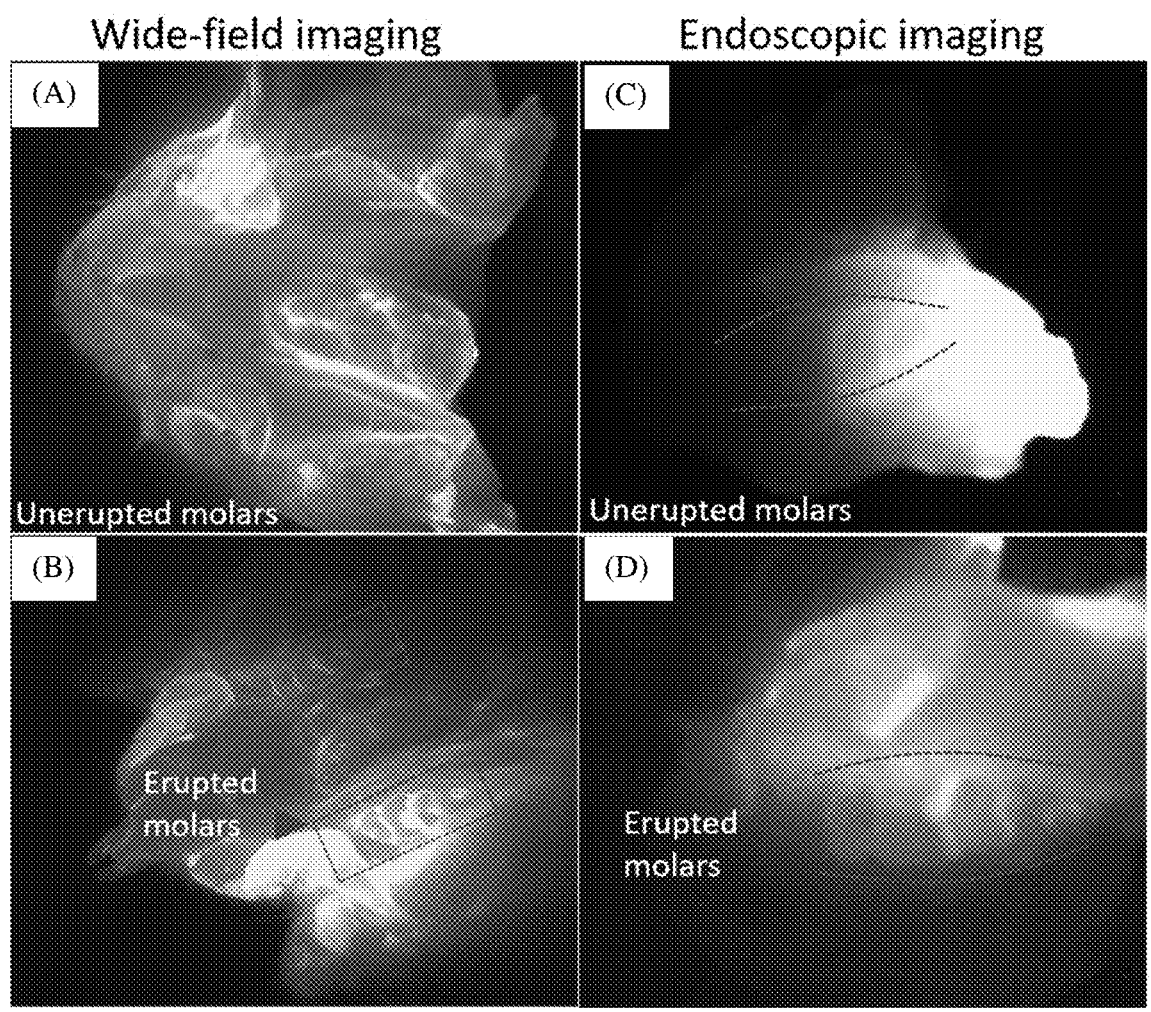
FIG. 3 shows ICG-assisted NIR images of unerupted and erupted molars. (A) shows an ICG-assisted NIR image of unerupted molars with 1 minute in vivo mouthwash under wide-filed imaging; (B) shows an ICG-assisted NIR image of erupted molars with 1 minute in vivo mouthwash under wide-field imaging; (C) shows ICG-assisted NIR images of unerupted molars with 1 minute in vivo mouthwash under endoscopic imaging; (D) shows ICG-assisted NIR images of erupted molars with 1 minute in vivo mouthwash under endoscopic imaging.

To learn the difference between mouthwash and subcutaneous injection, one P31 rat (erupted molars) and one P14 rat (unerupted molars) were injected with ICG solution. The erupted molars (of P31 rat) were clearly observable at a short imaging window (10 minutes). Each cusp of the first and second molars was distinguished, but after 24 hours of ICG injection, no dental structures could be observed. For the unerupted molars (of P14 rats), although the molars were still embedded in the bony crypts, the three-cusps profiles of the first molars were easily recognized from the ICG-assisted dental images. At the short imaging window, the molar regions were relatively darker than the surrounding tissues. However, at a long imaging window (48 hours), the unerupted molar could still be observed from ICG-assisted dental images, and with even more prominent contrast the surrounding tissues became darker, while the molar regions remained bright (FIG. 3). Injection performed better than mouthwash to the unerupted molars via wide-field imaging (FIG. 3(A) and FIG. 4(B)); while they were similar via endoscopic imaging (FIG. 3(C) and FIG. 4(C)).

Figure 4:
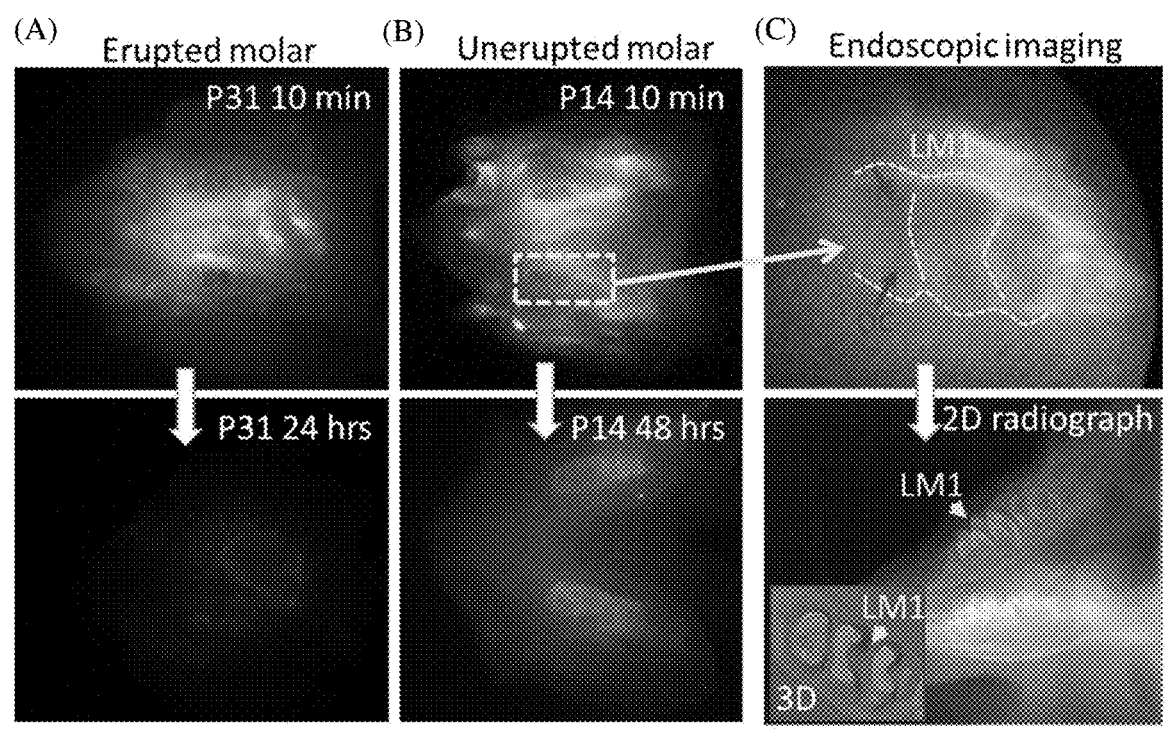
FIG. 4 shows ICG-assisted NIR dental imaging of erupted and unerupted molars (subcutaneous injection) in various imaging windows. (A) shows the ICG-assisted NIR images of the erupted molars at 10 min vs. 24 hours after ICG administration; (B) shows the ICG-assisted NIR images of the unerupted molars at 10 min vs. 48 hours after ICG administration; (C) shows the unerupted molar under ICG-assisted endoscopic dental imaging vs 2D and 3D radiograph. LM1: left first molar; LC: lingual cusps; OC: occlusal cusps.

For X-ray imaging, each cusp of the first molar was distinguishable, but lingual and occlusal cusps were overlapped together in the 2D radiography. From the 3D X-ray image, the morphological structures of the first molars were well-reconstructed in the CT slices; both lingual and occlusal cusps were distinguished (FIG. 4). From the endoscopic dental images, the similar profiles of the first molars were able to be identified; the outlines of the three cusps (particularly the second and the third cusps) were also similar to the profile in the 3D X-ray images (FIG. 4).

ICG-Mouthwash Imaging of Human and Rat Extracted Teeth

Figure 5:
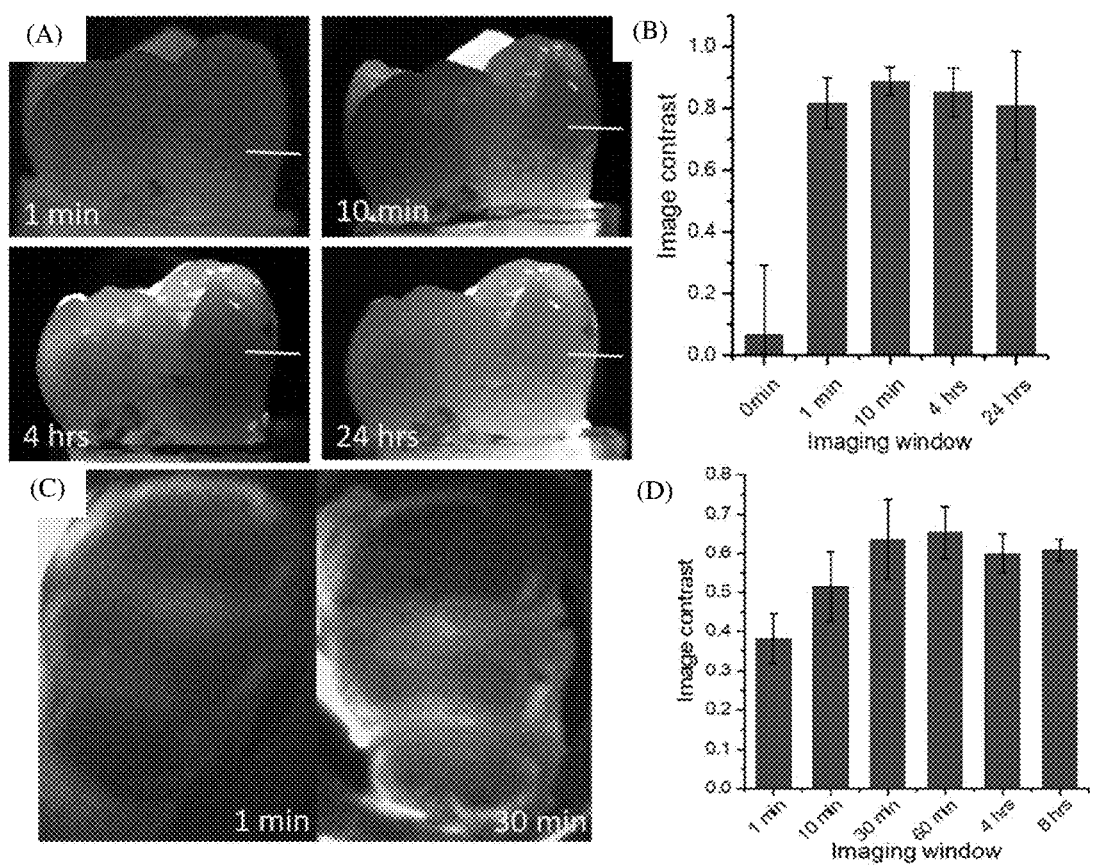
FIG. 5 shows the effect of ICG ex vivo mouthwash (immersion) time on NIR dental imaging and the image contrast of ICG-assisted dental images under different ICG immersion time. (A) shows the effect of ICG ex vivo mouthwash (immersion) time on NIR dental imaging of an extracted human tooth. This image was enhanced for visualization purposes only; the calculations of contrast and intensity were based on unenhanced pictures; (B) shows the image contrast of ICG-assisted dental images under different ICG immersion time of the extracted human tooth; (C) shows the effect of ICG ex vivo mouthwash (immersion) time on NIR dental imaging of an extracted rat molar. This image was not enhanced; (D) shows the image contrast of ICG-assisted dental images under different ICG immersion time of the extract rat molar.

Previous work demonstrated the feasibility of imaging human teeth with ICG-assisted dental imaging and its efficacy was compared to X-ray dental imaging.[31, 36] In this work, imaging window and spectral characteristics were systematically investigated and optimized. The profiles of the human tooth were able to be observed in as short as only 1 minute of ICG immersion, which is an ex vivo mouthwash delivery of dye (FIG. 5(A)-(C)). With increasing immersion time (4 and 24 hours), the profiles of the teeth became clearer than that of the 10 min-immersion. FIG. 5(C) shows the effect of ICG ex vivo mouthwash with the extracted single rat first molar (occlusal view). The molar became distinguishable after 30 min-immersion. The ICG concentration of immersion solution was 50 μM, the same as with human teeth.

The tooth with ICG immersion had a larger image contrast than that of the tooth without ICG immersion (FIG. 5(B)). There was almost no substantial difference of image contrast among the different imaging windows from 1 minute to 24 hours; the profile of the tooth became clearer with longer immersion time. The extracted rat tooth showed a similar tendency and the contrast kept stable around 0.6 (FIG. 5(D)), which was 0.2 less than that of the human teeth.

Enamel-Dentin Identification and Crack/Caries Detection

Figure 6:
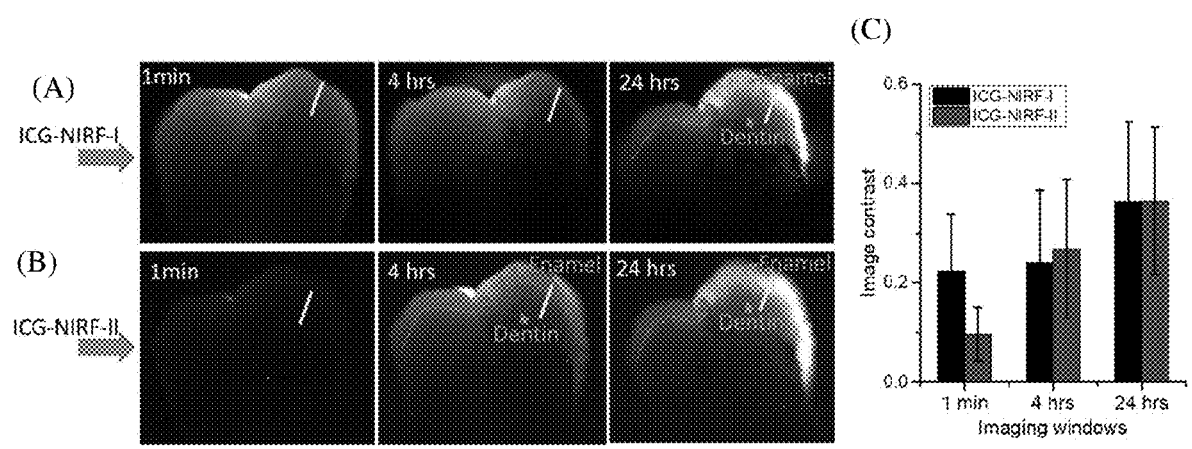
FIG. 6 shows human enamel-dentin differentiation in the first and second NIR windows. (A) shows the ICG-NIFI-I images acquired at different ICG immersion times. ICG-NIRF-I: ICG-assisted near-infrared fluorescence dental imaging in the first NIR windows (700-950 nm); (B) shows the ICG-NIFI-II images acquired at different ICG immersion times. ICG-NIRF-II: ICG-assisted near-infrared fluorescence dental imaging in the second NIR windows (1,000-1,700 nm); (C) shows the image contrast of the enamel and dentin under different ICG immersion times.

At short imaging window (1 minute), the dentin and enamel could not be distinguished from each other in the dental images of ICG-NIRF-II (ICG-assisted NIR dental imaging) in the second NIR windows (1,000-1,700 nm), but ICG-NIRF-I (700-950 nm) had much clearer profiles of the human tooth than that of ICG-NIRF-II (FIG. 6(A)). After 4 hours of ICG immersion, the enamel became slightly transparent and was easy to identify from the dentin under ICG-NIRF-II imaging. After immersion into ICG solution for 24 hours, both ICG-NIRF-I and ICG-NIRF-II showed a clear boundary between the dentin and enamel.

Image contrast of the dentin and enamel increased with the immersion time as shown in FIG. 6(C). Tooth imaging at 24 hours after ICG immersion, in particular, had a much larger image contrast than that of the short immersion time (1 minute and 4 hours), and there was almost no difference between ICG-NIRF-I and ICG-NIRF-II.

Figure 7:
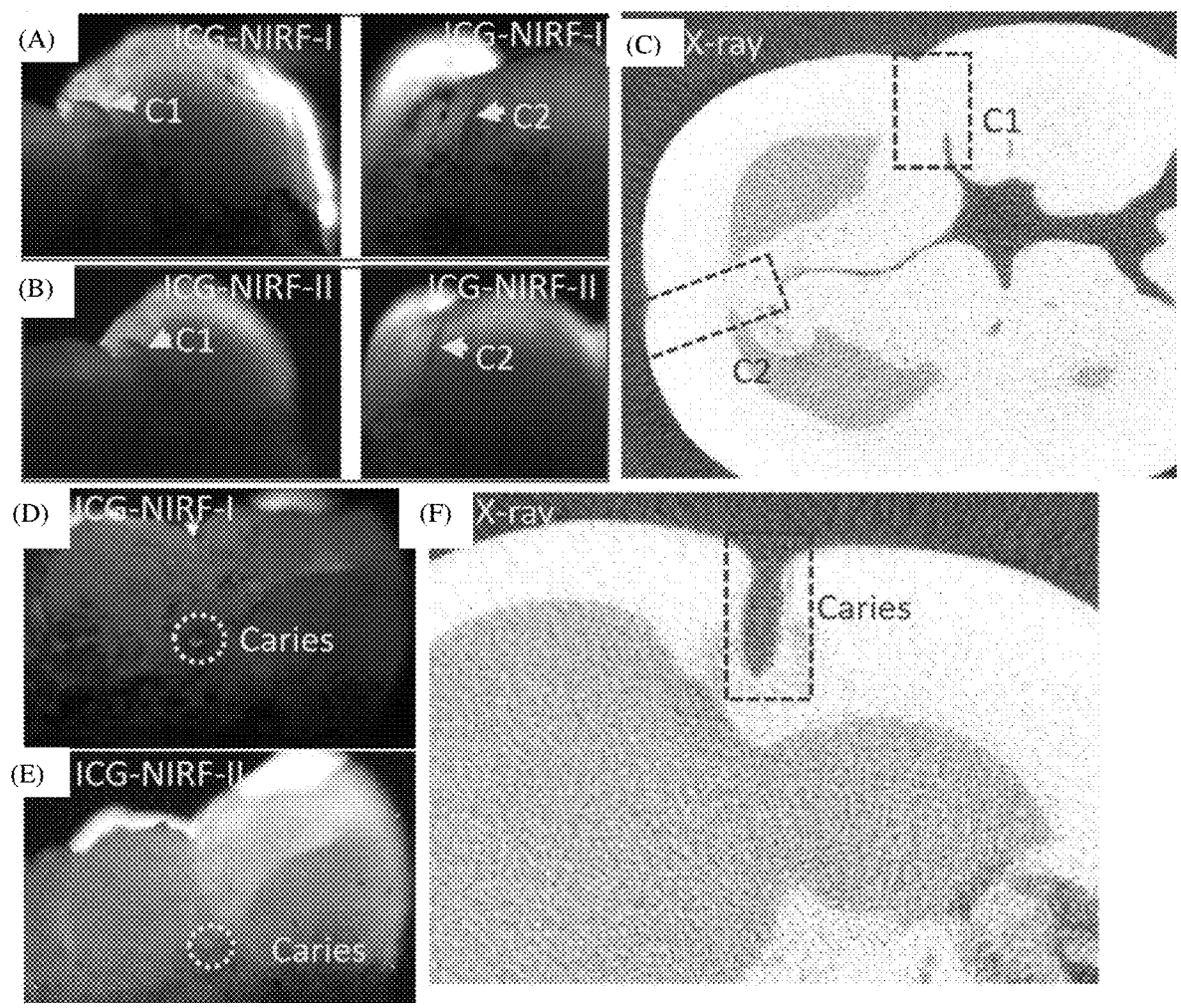
FIG. 7 shows image cracks and caries lesion in the first and second NIR windows. (A) shows ICG-NIRF-I dental imaging to detect cracks. C1: crack 1; C2: crack 2; (B) shows ICG-NIRF-II dental imaging to detect cracks. C1: crack 1; C2: crack 2; (C) shows the cracks that dental X-ray fails to recognize. C1: crack 1; C2: crack 2; (D) shows caries in ICG-NIRF-I dental imaging; (E) shows caries in ICG-NIRF-II dental imaging; (F) shows caries as compared to dental X-ray imaging.
Figure 8:
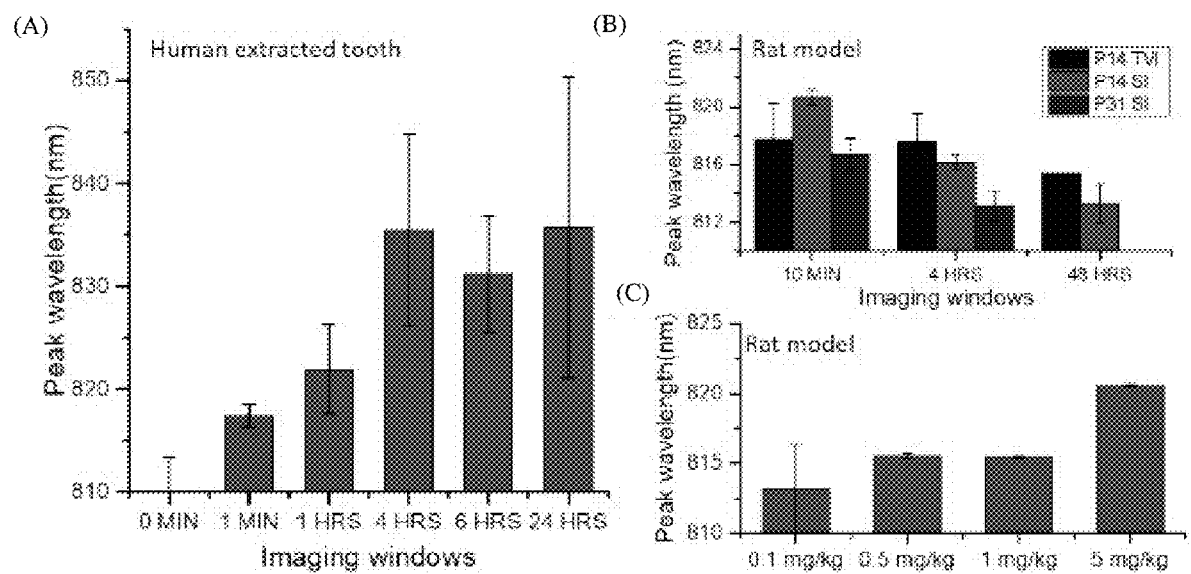
FIG. 8 shows spectral characteristics of ICG-assisted NIR dental imaging of human extracted teeth and rat molars. (A) shows that the peak wavelength of the spectrum of the human extracted teeth changes with ICG immersion time (N=3); (B) shows the peak wavelength of the spectrum of the rat teeth changes with imaging windows (N=2). SI: subcutaneous injection; TVI: tail vein injection; (C) shows the peak wavelength of the spectrum of the rat teeth changes with ICG injection dosage (N=2).

Cracks and caries were easily found in both the first and second NIR windows, that prevalent dental X-ray and CT[29, 36] fail to detect (FIG. 7). Neither of the cracks could be observed from the corresponding micro-CT slices (FIG. 7(C)), but both cracks were easily recognized from the first and second NIR windows.

Caries lesions were much easier to be observed through X-ray imaging (FIG. 7(F)), especially the depth of a caries lesion could (FIGS. 7(D) and (E)), be clearly seen, when compared to the cracks. In ICG-NIRF-I and ICG-NIRF-II imaging it was easy to identify the caries lesion from the NIR dental images. Particularly, the caries lesion became much brighter than the surrounding dental structures under ICG-NIRF-I imaging (FIG. 7(D)).

The Spectral Characteristics of ICG Concentration and the Imaging Windows

For the human teeth shown in FIG. 7(A), ICG immersion times affected the spectral characteristics of the tooth fluorescence, such as peak wavelengths. For the first four hours, the peak wavelength increased from 817 nm to 836 nm; then decreased slightly to hold around 833 nm. Regarding the rat model (FIG. 7(B)), the influence of the injection methods (subcutaneous injection and tail vein injection) and imaging window (at 10 minutes, 4 hours and 48 hours) on a shift of peak wavelengths were investigated. The peak wavelength decreased with the imaging windows in both injection methods. Furthermore, tail vein injection had a smaller peak wavelength after 10 minutes of ICG injection than the subcutaneous injection, but became larger after 4 hours of injection; the erupted molar (of P31 rats) had a smaller peak wavelength than the unerupted molar (of P14 rats).

Additionally, the peak wavelength was influenced by the doses of ICG injection at the imaging window of 4 hours (FIG. 7(C)). Increased peak wavelength was observed with increased ICG injection dose: the peak wavelength was about 820 nm for 5 mg/kg and 813 nm for 0.1 mg/kg. The doses of 0.5 and 1 mg/kg almost showed the same peak wavelength at about 815 nm. However, from ICG-NIRF-I NIR images (FIG. 9), a high injection dose would make it easier to obtain a clearer profile of the dental structures as compared to a low dose.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1. Sheiham, A. 2005. "Oral health, general health and quality of life". In. SciELO Public Health.
2. Yadav, K. & S. Prakash. 2016. Dental caries: A review. *Asian Journal of Biomedical and Pharmaceutical Sciences.* 6: 01.
3. Sener., I., A. Turer., C. Bereket., et al. 2013. Non-Syndromic Familial Unerupted Teeth A Rare Contidion. *Cumhuriyet Dental Journal.* 18: 359-363.
4. Guerrero, M. E., M. Shahbazian, G. Elsiena Bekkering, et al. 2011. The diagnostic efficacy of cone beam CT for impacted teeth and associated features: a systematic review. *J Oral Rehabil.* 38: 208-216.
5. Pereira, I. F., F. Z. M. Santiago, A. C. Sette-Dias, et al. 2017. Taking advantage of an unerupted third molar: a case report. *Dental Press J Orthod.* 22: 97-101.
6. Fried, W. A., J. C. Simon, S. Lucas, et al. 2014. Near-IR imaging of cracks in teeth. *Proc SPIE Int Soc Opt Eng.* 8929: 89290Q.
7. Kahler, W. 2008. The cracked tooth conundrum: terminology, classification, diagnosis, and management. *Am J Dent.* 21: 275-282.
8. Seo, D. G., Y. A. Yi, S. J. Shin, et al. 2012. Analysis of factors associated with cracked teeth. *J Endod.* 38: 288-292.
9. Hasan, S., K. Singh & N. Salati. 2015. Cracked tooth syndrome: Overview of literature. *Int J Appl Basic Med Res.* 5: 164-168.
10. Mathew, S., B. Thangavel, C. A. Mathew, et al. 2012. Diagnosis of cracked tooth syndrome. *J Pharm Bioallied Sci.* 4: S242-244.
11. Kawase, S., Y. Okada, K. Isono, et al. 2019. Cerebral abscess following the self-extraction of teeth in patient with Ebstein's anomaly: a case report. *BMC Oral Health.* 19: 200.
12. Vandenberghe, B., R. Jacobs & H. Bosmans. 2010. Modern dental imaging: a review of the current technology and clinical applications in dental practice. *Eur Radiol.* 20: 2637-2655.
13. Association, A. D. 2012. Dental radiographic examinations: recommendations for patient selection and limiting radiation exposure. *Chicago: ADA.*
14. Kiljunen, T., T. Kaasalainen, A. Suomalainen, et al. 2015. Dental cone beam CT: A review. *Phys Med.* 31: 844-860.
15. Shah, N., N. Bansal & A. Logani. 2014. Recent advances in imaging technologies in dentistry. *World J Radiol.* 6: 794-807.
16. Tymofiyeva, O., K. Rottner, P. M. Jakob, et al. 2010. Three-dimensional localization of impacted teeth using magnetic resonance imaging. *Clin OralInvestig.* 14: 169-176.
17. Bolouri, C., M. Merwald, M. W. Huellner, et al. 2013. Performance of orthopantomography, planar scintigraphy, CT alone and SPECT/CT in patients with suspected osteomyelitis of the jaw. *Eur J Nucl Med Mol Imaging.* 40: 411-417.

18. Erten, H., M. Ugtasli, Z. Akarslan, et al. 2006. Restorative treatment decision making with unaided visual examination, intraoral camera and operating microscope. *Operative dentistry.* 31: 55-59.
19. Staninec, M., S. M. Douglas, C. L. Darling, et al. 2011. Non-destructive clinical assessment of occlusal caries lesions using near-IR imaging methods. *Lasers Surg Med.* 43: 951-959.
20. Jones, R. S., G. D. Huynh, G. C. Jones, et al. 2003. Near-infrared transillumination at 1310-nm for the imaging of early dental decay. *Opt Express.* 11: 2259-2265.
21. Simon, J. C., S. A. Lucas, M. Staninec, et al. 2014. Transillumination and reflectance probes for in vivo near-IR imaging of dental caries. *Proc SPIE Int Soc Opt Eng.* 8929: 89290D.
22. Usenik, P., M. Burmen, A. Fidler, et al. 2012. Automated Classification and Visualization of Healthy and Diseased Hard Dental Tissues by Near-Infrared Hyperspectral Imaging. *Applied Spectroscopy.* 66: 1067-1074.
23. Staninec, M., C. Lee, C. L. Darling, et al. 2010. In vivo near-IR imaging of approximal dental decay at 1,310 nm. *Lasers Surg Med.* 42: 292-298.
24. Chung, S., D. Fried, M. Staninec, et al. 2011. Multispectral near-IR reflectance and transillumination imaging of teeth. *Biomed Opt Express.* 2: 2804-2814.
25. Chung, S., D. Fried, M. Staninec, et al. 2011. Near infrared imaging of teeth at wavelengths between 1200 and 1600 nm. *Proc SPIE Int Soc Opt Eng.* 7884.
26. Wu, J. & D. Fried. 2009. High contrast near-infrared polarized reflectance images of demineralization on tooth buccal and occlusal surfaces at lambda λ=1310-nm. *Lasers Surg Med.* 41: 208-213.
27. Buhler, C. M., P. Ngaotheppitak & D. Fried. 2005. Imaging of occlusal dental caries (decay) with near-IR light at 1310-nm. *Opt Express.* 13: 573-582.
28. Lee, C., D. Lee, C. L. Darling, et al. 2010. Nondestructive assessment of the severity of occlusal caries lesions with near-infrared imaging at 1310 nm. *J Biomed Opt.* 15: 047011.
29. Li, Z., S. Yao, J. Xu, et al. 2018. Cover Image, Volume 1421, Issue 1. *Ann N Y Acad Sci.* 1421: i-i.
30. Li, Z., S. Yao, J. Xu, et al. 2018. Endoscopic near-infrared dental imaging with indocyanine green: a pilot study. *Ann NY Acad Sci.* 1421: 88-96.
31. Li, Z., S. Yao & J. Xu. 2019. Indocyanine-green-assisted near-infrared dental imaging—the feasibility of in vivo imaging and the optimization of imaging conditions. *Scientific reports.* 9: 8238.
32. Li, Z., W. Zaid, T. Hartzler, et al. 2019. Indocyanine green-assisted dental imaging in the first and second near-infrared windows as compared with X-ray imaging. *Ann NY Acad Sci.* i: 1-10.
33. Information, C. f. S. 2019. Mouthwash (Mouthrinse). Accessed Mar. 27, 2019. https://www.ada.org/en/member-center/oral-health-topics/mouthrinse#
34. Dubey, R. & K. G. Dubey. 2018. Evaluation of novel mouthwash on dental remineralization. *Evaluation.* 4: 167-169.
35. Bagchi, S., S. Saha, G. Jagannath, et al. 2015. Evaluation of efficacy of a commercially available herbal mouthwash on dental plaque and gingivitis: A double-blinded parallel randomized controlled trial. *Journal of Indian Association of Public Health Dentistry.* 13: 222.
36. Li, Z., W. Zaid, T. Hartzler, et al. 2019. Cover Image, Volume 1448, Issue 1. *Ann NY Acad Sci.* 1448: i-i.
37. Banerji, S., S. B. Mehta & B. J. Millar. 2010. Cracked tooth syndrome. Part 1: aetiology and diagnosis. *Br Dent J.* 208: 459-463.
38. Lee, S. H., J. J. Lee, H. J. Chung, et al. 2016. Dental optical coherence tomography: new potential diagnostic system for cracked-tooth syndrome. *Surg Radiol Anat.* 38: 49-54.
39. Simon, J. C., A. L. S, R. C. Lee, et al. 2016. Near-infrared imaging of secondary caries lesions around composite restorations at wavelengths from 1300-1700-nm. *Dent Mater.* 32: 587-595.

We claim:

1. A method for identifying a crack or a caries lesion in a tooth by fluorescent endoscopic dental imaging, the method comprising:
   orally administering to a subject a mouthwash comprising indocyanine green (ICG) at concentration of 50 µM-1.3 mM and a liquid base;
   waiting a predetermined period of time;
   removing excess mouthwash from the subject;
   illuminating the subject with visible or near-infrared light;
   capturing fluorescent light from the subject to create an image;
   analyzing the fluorescent light to create a spectroscopic signal displaying the image and
   detecting the presence or absence of the crack or the caries lesion in the tooth.
2. The method for fluorescent endoscopic dental imaging according to claim 1, wherein the liquid base comprises water, or medical normal saline solution made from sodium chloride.
3. The method for fluorescent endoscopic dental imaging according to claim 1, wherein the liquid base comprises at least one of ethanol, menthol, sorbitol, glycerin, and xylitol.
4. The method for fluorescent endoscopic dental imaging according to claim 1, wherein the predetermined period of time is 1-2 minutes.
5. The method for fluorescent endoscopic dental imaging according to claim 1, wherein administering the mouthwash further comprises instructing the subject not to ingest the mouthwash.
6. The method for fluorescent endoscopic dental imaging according to claim 1, wherein the method does not include administering a contrast agent subcutaneously or intravenously.
7. The method for fluorescent endoscopic dental imaging according to claim 1, wherein the amount of mouthwash is 8-400 ml for a human subject to reach an effective dosage of dye of 0.1-5 mg/kg ICG, and wherein the method comprises illuminating the subject with near-infrared light.
8. The method for fluorescent endoscopic dental imaging according to claim 1, wherein the image comprises a two-dimensional near-infrared dental image of the subject.
9. The method for fluorescent endoscopic dental imaging according to claim 1, further comprising displaying spectroscopic data corresponding to the spectroscopic signal.
10. The method for fluorescent endoscopic dental imaging according to claim 1, wherein the method does not use ionizing-radiation materials.
11. The method for fluorescent endoscopic dental imaging according to claim 1, further comprising analyzing the fluorescent light to identify one of the crack or the caries lesion in the tooth of the subject.
12. The method for fluorescent endoscopic dental imaging according to claim 1, comprising illuminating the subject with near-infrared light.

13. The method for fluorescent endoscopic dental imaging according to claim 1, wherein the imaging is done in a first near-infrared (NIR) window (700-950 nm), a second NIR window (1000-1700 nm), or a combination thereof.

14. The method for fluorescent endoscopic dental imaging according to claim 13, wherein the imaging is done in the first near-infrared (NIR) window (700-950 nm).

15. The method for fluorescent endoscopic dental imaging according to claim 13, wherein the imaging is done in the second NIR window (1000-1700 nm).

16. The method for fluorescent endoscopic dental imaging according to claim 1, further comprising analyzing the fluorescent light to identify an enamel crack in the tooth of the subject.

* * * * *